(12) United States Patent
Lerat et al.

(10) Patent No.: US 10,874,525 B2
(45) Date of Patent: Dec. 29, 2020

(54) SURGICAL INSTRUMENT FOR KNEE BALANCING

(71) Applicant: AMPLITUDE, Valence (FR)

(72) Inventors: Bernard Lerat, Valence (FR); Sylvain Thibaut, Saint Marcel les Valences (FR); Nicolas Goubet, Bernin (FR)

(73) Assignee: AMPLITUDE, Valence (FR)

( * ) Notice: Subject to any disclaimer, the term of this patent is extended or adjusted under 35 U.S.C. 154(b) by 127 days.

(21) Appl. No.: 15/996,395

(22) Filed: Jun. 1, 2018

(65) Prior Publication Data

US 2019/0358056 A1 Nov. 28, 2019

(30) Foreign Application Priority Data

May 24, 2018 (FR) ..................... 18 54341

(51) Int. Cl.
*A61F 2/46* (2006.01)

(52) U.S. Cl.
CPC ...... *A61F 2/461* (2013.01); *A61F 2002/4628* (2013.01); *A61F 2002/4658* (2013.01); *A61F 2002/4666* (2013.01); *A61F 2002/4668* (2013.01); *A61F 2002/4687* (2013.01)

(58) Field of Classification Search
CPC ............................ A61F 2/461; A61B 17/1764
See application file for complete search history.

(56) References Cited

U.S. PATENT DOCUMENTS

| | | | | |
|---|---|---|---|---|
| 9,271,756 B2* | 3/2016 | van der Walt | ......... | A61B 17/56 |
| 9,592,133 B2* | 3/2017 | Toler | .......... | A61F 2/38 |
| 2004/0122441 A1* | 6/2004 | Muratsu | ............. | A61B 17/0206 606/102 |
| 2006/0241569 A1* | 10/2006 | DiSilvestro | ............. | A61F 2/461 606/1 |
| 2011/0046685 A1* | 2/2011 | Faure | .................... | A61F 2/4657 606/86 R |
| 2011/0093081 A1* | 4/2011 | Chana | ................ | A61B 17/1764 623/20.14 |

(Continued)

FOREIGN PATENT DOCUMENTS

| | | |
|---|---|---|
| EP | 0809969 A2 | 12/1997 |
| EP | 0809969 A3 | 7/1998 |

(Continued)

*Primary Examiner* — Zade Coley
(74) *Attorney, Agent, or Firm* — Burris Law, PLLC (57) ABSTRACT

A surgical instrument (1) for knee balancing, comprising:
- a static tibial element (2) including a base and a tibial paddle (21);
- a femoral element (3) including a femoral paddle (31) and a femoral arm;
- a movable element (4) including a guide (40) movable in translation on the base according to a longitudinal axis (AL), wherein the femoral element is pivotally mounted on said movable element according to an anterior-posterior axis (AP), and a transverse arm;
- a system (5) for setting the mobility of said guide in order to provide a distraction function;
- a reversible blocking system coupled between the transverse arm and the femoral arm to pivotally immobilize the femoral element with respect to the movable element in a reversible manner in order to set the pivot angle of the femoral paddle with respect to the tibial paddle at different angle values.

13 Claims, 5 Drawing Sheets

(56) References Cited

U.S. PATENT DOCUMENTS

| | | | |
|---|---|---|---|
| 2014/0288563 A1* | 9/2014 | Claypool | A61B 17/155 |
| | | | 606/88 |
| 2016/0135825 A1* | 5/2016 | Toler | A61B 17/155 |
| | | | 606/88 |
| 2017/0333018 A1* | 11/2017 | Sehat | A61B 17/1764 |
| 2018/0296232 A1* | 10/2018 | Nielsen | A61B 5/4528 |

FOREIGN PATENT DOCUMENTS

| | | |
|---|---|---|
| EP | 2277460 A1 | 1/2011 |
| WO | 2010111678 A2 | 9/2010 |
| WO | 2010111678 A3 | 4/2013 |

* cited by examiner

SURGICAL INSTRUMENT FOR KNEE BALANCING

The present invention relates to a surgical instrument for knee balancing in the context of a preparation of surgical setting of a total knee prosthesis.

During the setting of a total knee prosthesis, the surgeon should pay particular attention to the following two points:
the alignment of the leg set in an extended state wherein the hip center, the knee center and the ankle center tend to be completely or partially aligned after the surgery;
the ligament tension at the level of the medial and lateral ligaments in order to guarantee a proper stability of the joint.

More particularly, the invention relates to this second point by proposing a surgical instrument allowing achieving a ligament balance in preparation for the setting of a total knee prosthesis.

Currently, it is known to manage this second point by tensioning the joint of the knee with wedges or with a mechanical tensioner and then manually assessing the ligament tension, the obtained result then being subjective.

The state of the art may be illustrated by the teachings of the documents U.S. Pat. No. 9,592,133 and US2016/0135825 each disclosing a surgical instrument comprising a tibial paddle and a femoral paddle pivoting relative to the tibial paddle which is static, as well as a setting system providing a distraction function by enabling a setting of the spacing between the femoral paddle and the tibial paddle.

With this type of instrument, it is then possible to make the femoral paddle pivot relative to the tibial paddle, so that the surgeon could then perform *varus*-valgus movements in order to obtain an estimate of the stability of the joint. However, it should be noted that the pivoting of the femoral paddle relative to the tibial paddle is free, which while enabling the instrument to always be in a situation wherein the medial tension is equal to the lateral tension, has the drawback of not enabling an immobilization of the pivot angle between the femoral paddle and the tibial paddle at different values, except a possible locking of the pivot angle restricted to the sole value of zero degree in order to immobilize a parallelism between the femoral paddle and the tibial paddle.

The present invention aims in particular at solving all or part of the aforementioned drawback by proposing a surgical instrument which enables both a free adjustment of the ligament balance when the leg is set in a bent state and an objective control of the ligament balance when the leg is set in an extended state.

Another object of the invention is to enable a positioning of a guide element comprising several guide orifices for drills in the femur, in order to enable the completion of the femoral cuts directly based on the controlled balance.

To this end, it proposes a surgical instrument for knee balancing in the context of a preparation of surgical setting of a total knee prosthesis, said surgical instrument comprising:
a static tibial element including a base secured to a tibial paddle intended to bear on a resected proximal end of the tibia;
a femoral element including a femoral paddle intended to bear on the distal or posterior condyles of the femur or on a resected distal end of the femur or on a compensation wedge;
a movable element including a guide mounted movable in translation on the base of the static tibial element according to a longitudinal axis, and in which the femoral element is pivotally mounted on said movable element according to an anterior-posterior axis, so that the femoral paddle pivots about said anterior-posterior axis relative to the tibial paddle which is static;
a setting system coupled between the guide of the movable element and the base of the static tibial element for setting the mobility of said guide relative to said base in order to provide a distraction function while enabling a setting of the spacing between the femoral paddle and the tibial paddle;
wherein the movable element comprises a transverse arm secured to the guide, and the femoral element comprises a femoral arm secured to the femoral paddle;
and wherein the surgical instrument further comprises a reversible blocking system coupled between the transverse arm of the movable element and the femoral arm of the femoral element to pivotally immobilize the femoral element with respect to the movable element in a reversible manner in order to set the pivot angle of the femoral paddle with respect to the tibial paddle at different pivot angle values.

Thus, the invention allows objectivizing the rotational angular positioning of the prosthetic condyle during setting of a total knee prosthesis with a conventional instrumentation. During tensioning, the femoral paddle freely pivots relative to the tibial paddle, which tends to balance the forces. Afterwards, the surgeon may be satisfied with the mechanically-obtained equilibrium or he may adjust the balance by pivoting the femoral arm, and therefore the femoral paddle, the adjustment thereby obtained may finally be fixed by means of the reversible blocking system so as to pivotally lock the femoral paddle, at a zero angle or at different other angles depending on the ligament adjustment pursued by the surgeon.

Advantageously, the transverse arm of the movable element terminates in a free end provided with a first reference element, and the femoral arm of the femoral element terminates in a free end provided with a second reference element, wherein the first reference element and the second reference element comprise a scale of graduations distributed around the anterior-posterior axis and a reference marking visually matching with the graduated scale, so as to measure a value of the pivot angle of the femoral paddle with respect to the tibial paddle.

In a particular embodiment, the reversible blocking system comprises:
a jaw which is provided on a free end of the femoral arm, and which comprises two clamps opposite each other and movable between a clamped position and an unclamped position;
a rail which is provided on a free end of the transverse arm of the movable element and which is engaged into the jaw between the two clamps;
a clamping element cooperating with the jaw so as to displace the clamps between the clamped position and the unclamped position, such that, when in the clamped position, the femoral element is pivotally immobilized with respect to the movable element, and, when in the unclamped position, the femoral element is enabled to pivot relative to the movable element.

According to one feature, the jaw is formed by a slotted slide in which a slot is provided between the two clamps.

According to another feature, the clamping element comprises a clamping screw screwed into a clamping orifice which crosses the two clamps, so that screwing of the clamping screw displaces the clamps toward the clamped position and unscrewing of the clamping screw displaces the clamps toward the unclamped position.

Advantageously, the clamping screw and the clamping orifice extend according to a transverse axis orthogonal to the anterior-posterior axis, in order to be able to use a clamping screwdriver as a lever arm for making the femoral element pivot relative to the movable element when the clamps are in the unclamped position.

The invention also concerns a surgical system comprising such a surgical instrument, and further comprising a clamping screwdriver capable of cooperating with the clamping screw so as to ensure the screwing/unscrewing thereof, and also capable of forming a lever arm, once engaged with the clamping screw, in order to make the femoral element pivot relative to the movable element when the clamps are in the unclamped position.

Hence, the surgeon can adjust the balance through the lever arm effect offered by the clamping screwdriver engaged with the locking screw, the adjustment thereby obtained is fixed by screwing the locking screw until locking the rotation of the femoral paddle, at a zero angle or at different other angles depending on the ligament adjustment pursued by the surgeon.

According to a possibility of the invention, the guide comprises a rack formed by a series of teeth, and the setting system comprises a pinion which is pivotally mounted on the base of the static tibial element and which meshes with the rack.

According to another possibility of the invention, the setting system comprises a reversible locking mechanism coupled between the base of the static tibial element and the pinion so as to reversibly lock the rotation of the pinion and consequently the mobility of the guide relative to the base, in order to set the spacing between the femoral paddle and the tibial paddle.

In accordance with another feature of the invention, the reversible locking mechanism comprises a latch movably mounted on the base of the static tibial element between a locking position in which the latch cooperates with the pinion so as to rotatably lock it, and an unlocking position in which the latch does not cooperate with the pinion which is free to pivot.

The present invention also concerns the features hereinafter:
- the guide is provided with a first measuring element;
- the base of the static tibial element presents an aperture through which the first measuring element of the guide is visible, and said base further presents a second measuring element placed at the aperture side;
- the first measuring element and the second measuring element comprise a scale of graduations distributed along the longitudinal axis and a reference marking visually matching with the graduated scale, so as to measure a value of the spacing between the femoral paddle and the tibial paddle.

The invention also relates to a surgical system comprising a surgical instrument according to the invention, and further comprising a force sensor adapted to be removably placed on an upper face of the femoral paddle, opposite to a lower face which faces the tibial paddle, in order to detect one or several force(s) exerted by the condyles of the femur on the femoral paddle.

Advantageously, there is provided a measuring apparatus connected to the force sensor, via a wireless or wired link, and intended to receive the measurements performed by the force sensor, wherein said measuring apparatus is removably mounted on the base of the static tibial element.

Optionally, this measuring apparatus is provided with a display enabling a display of the measurements performed by the force sensor.

Alternatively, this measuring apparatus is connected to a remote display, in particular via a radio link, this remote display enabling a display of the measurements performed by the force sensor.

The invention also relates to a surgical system comprising a surgical instrument according to the invention and further comprising a guide element removably mounted on the base of the static tibial element, said guide element comprising several guide orifices for drills in the femur; such drills may then serve in fixing the femoral cutting guides.

Other features and advantages of the present invention will appear upon reading the detailed description hereinafter, of a non-limiting example of implementation, made with reference to the appended figures in which.

Referring to FIGS. 1, 3, 4, 11 and 12, a surgical instrument 1 according to an embodiment of the invention, mainly comprises the following elements:
- a static tibial element 2 including a base 20 secured to a tibial paddle 21 intended to bear on a resected end of the tibia;
- a femoral element 3 including a femoral paddle 31 intended to bear on the distal or posterior condyles of the femur or on a resected distal end of the femur;
- a movable element 4 including a guide 40 mounted movable in translation on the base 20 of the static tibial element 2 according to a longitudinal axis AL;
- a setting system 5 coupled between the guide 40 of the movable element 4 and the base 20 of the static tibial element 2 for setting the mobility of the guide 40 relative to the base 20 in order to provide a distraction function by enabling a setting of the spacing between the femoral paddle 31 and the tibial paddle 21, this spacing being considered according to the longitudinal axis AL.

Figures 5, 6, 7:
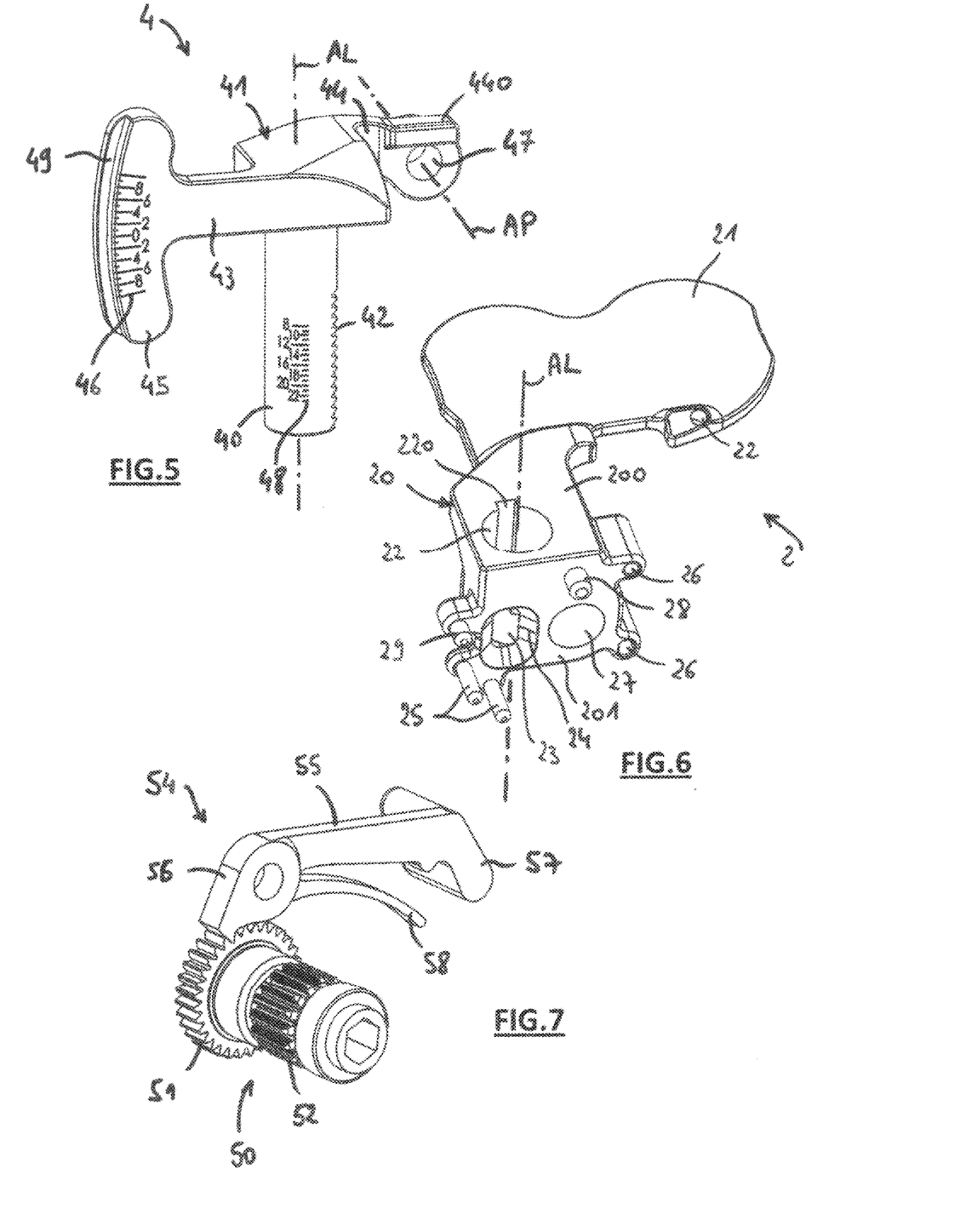
FIG. 5 is a schematic perspective view of a movable element alone for the surgical instrument shown in FIGS. 1, 3 and 4.
FIG. 6 is a schematic perspective view of a static tibial element alone for the surgical instrument shown in FIGS. 1, 3 and 4.
FIG. 7 is a schematic perspective view of a latch coupled to a pinion for the surgical instrument shown in FIGS. 1, 3 and 4.

Referring to FIG. 6, the static tibial element 2 is formed by an integral part and mainly comprises the base 20 and the tibial paddle 21. This static tibial element 2 is intended to be placed in a static manner on the resected end of the tibia and, as such, it may present a fastening orifice 22 formed at the periphery of the tibial paddle which allows stabilizing the static tibial element 2 on the resected end of the tibia with a nail.

The base 20 presents an upper face 200, parallel to the tibial paddle 21, and in which is formed a guide orifice 22 extending according to the longitudinal axis AL and crossing the base 20 throughout its entire height while opening onto a lower face, opposite to the upper face 200. This guide orifice 22 is intended to internally receive the guide 40 of the movable element 4, in order to slidingly guide it. This guide orifice 22 is provided with a groove 220 for preventing the rotation of the guide 40 inside the guide orifice 22.

The base 20 presents a front face 201 in which is formed an aperture 23 opening into the guide orifice 22 and through which the guide 40 is visible once in place inside the guide orifice 22. The base 20 further presents a marking 24 placed at the aperture 23 side; this marking 24 forming a second measuring element for measuring a value of the spacing between the femoral paddle 31 and the tibial paddle 21.

The base 20 also presents two pins 25, protruding from the front face 201, intended to enable a removable mounting of a measuring apparatus 9 (described later on) on the base 20.

The base 20 also presents two holding holes 26, opening into the front face 201, intended to enable a removable mounting of a guide element 6 (described later on) on the base 20. One of the two holding holes 26 has an oblong section whereas the other has a circular section.

The base 20 also presents a setting orifice 27, opening into the front face 201 and opening tangentially into the guide orifice 22, this setting orifice 27 extending according to a direction parallel to the anterior-posterior axis AP (described later on). This setting orifice 27 is intended to accommodate a pinion 50 of a setting system 5 (described later on).

The base 20 also presents a first finger 28, protruding from the front face 201, and disposed above the setting orifice 27, this first finger 28 being intended receive a pivot for a latch 54 of a reversible locking mechanism (described later on).

The base 20 also presents a second finger 29, protruding from the front face 201, and disposed above the two pins 25, this second finger 29 being intended to participate in holding the aforementioned latch 54 in a locking position, as described later on.

Referring to FIGS. 1, 3, 4, 11 and 12, the femoral element 3 is pivotally mounted on the movable element 4 according to an anterior-posterior axis AP, so that the femoral paddle 31 could pivot about this anterior-posterior axis AP relative to the tibial paddle 21 which is static.

Figure 1:
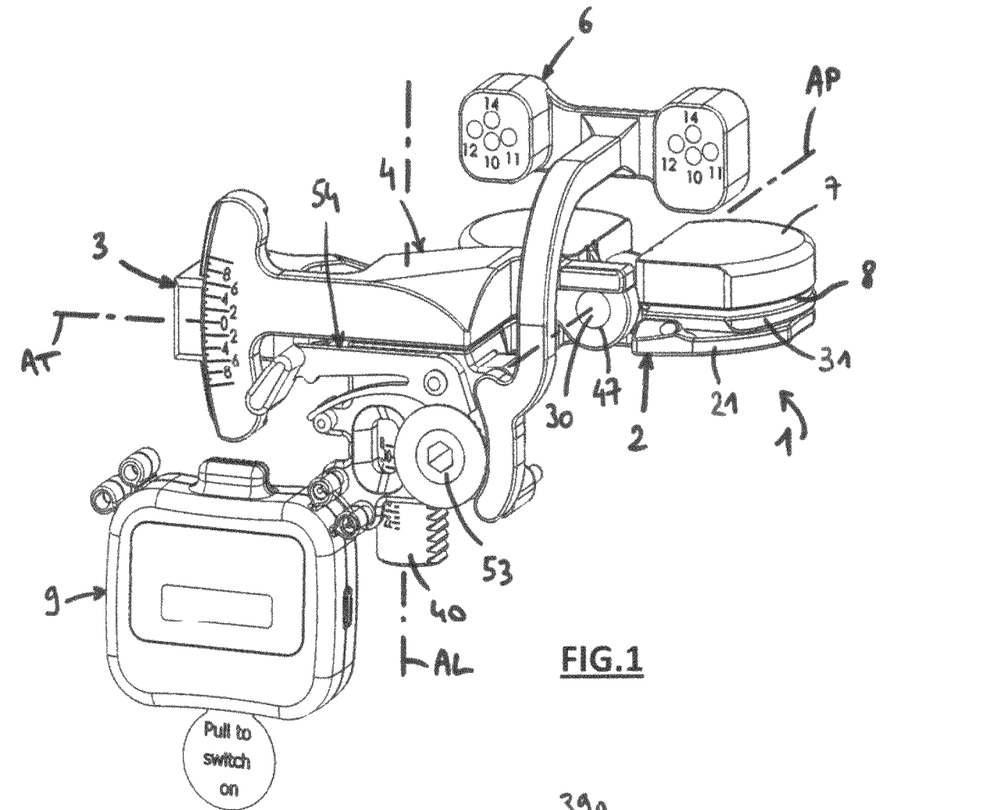
FIG. 1 is a schematic perspective view of an entire surgical system according to the invention, comprising a surgical instrument according to the invention, a force sensor, a measuring apparatus connected to the force sensor, a compensation wedge, and a guide element.
Figure 2:
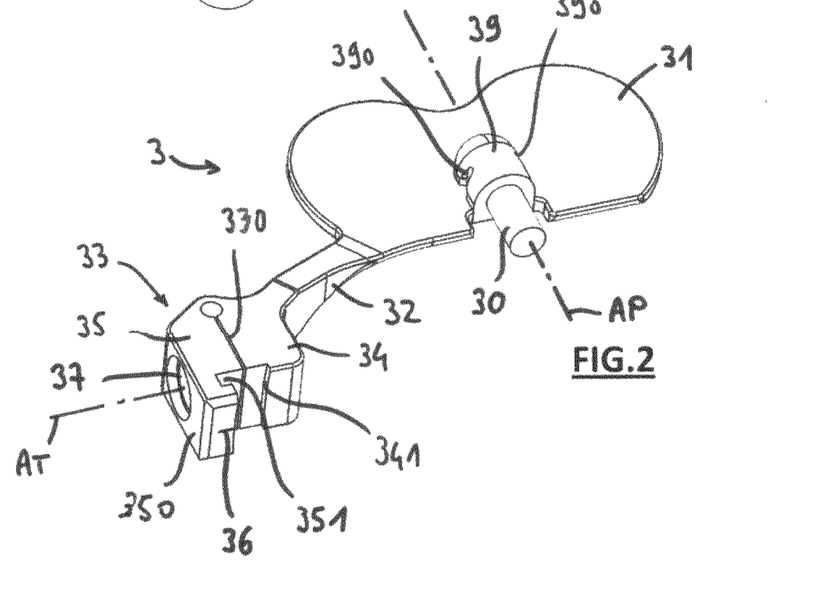
FIG. 2 is a schematic perspective view of a femoral element alone for the surgical instrument shown in FIG. 1.
Figure 3:
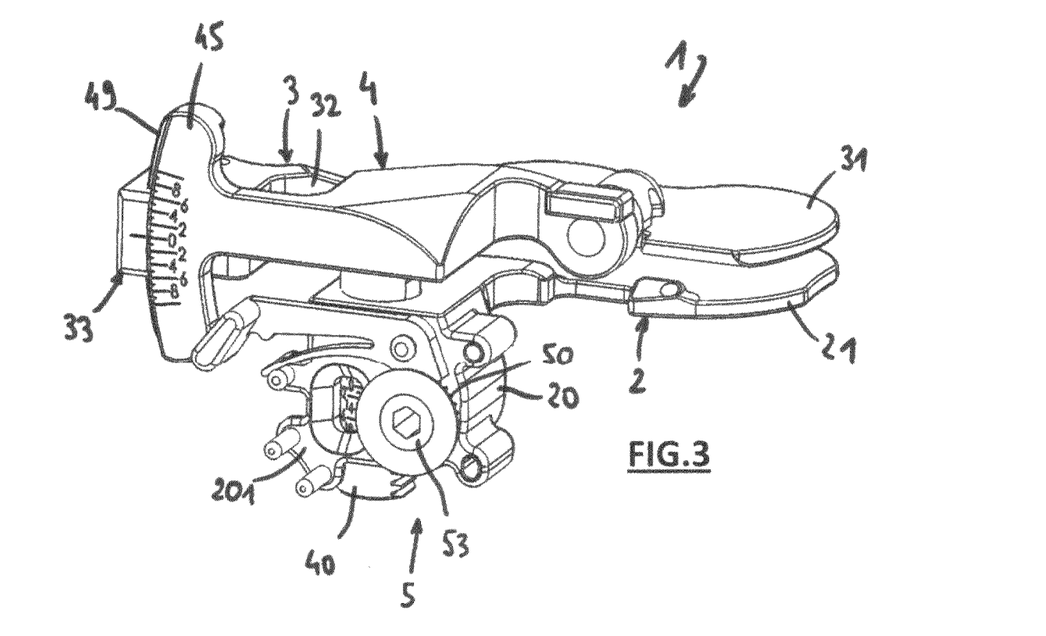
FIGS. 3 and 4 are schematic perspective views, according to two distinct view angles, of the surgical instrument shown in FIG. 1.
Figure 4:
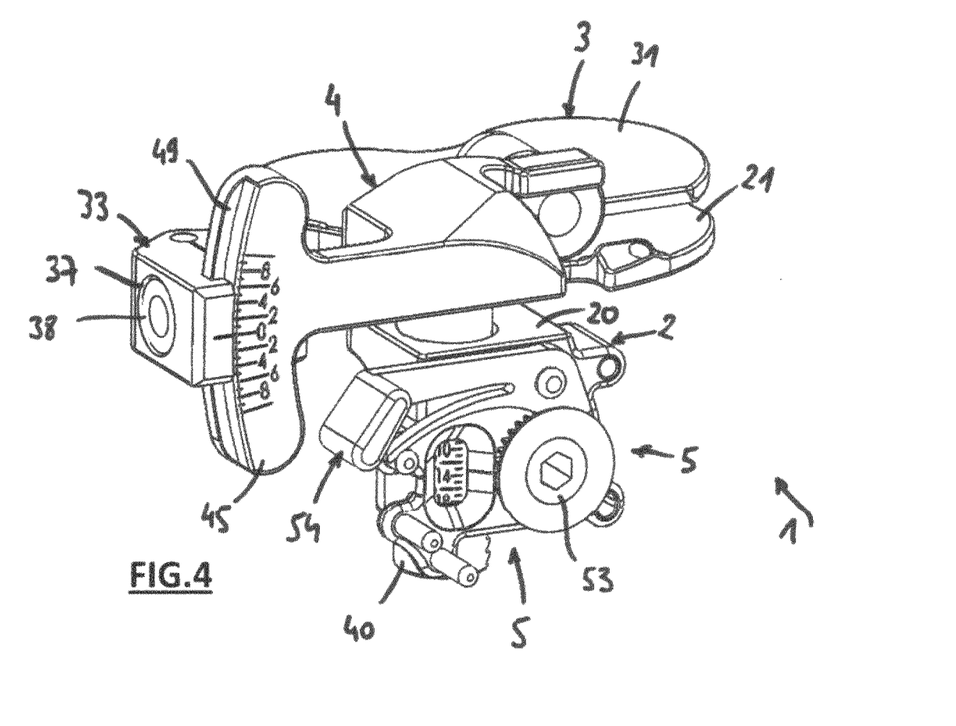

Referring to FIG. 2, the femoral element 3 is formed by an integral part and mainly comprises the femoral paddle 31, at the middle of which protrudes a pivot shaft 30 extending according to the anterior-posterior axis AP; this pivot shaft 30 forming the pivot for the femoral element 3.

Moreover, the femoral element 3 comprises a femoral arm 32 secured to the femoral paddle 31, wherein this femoral arm 32 extends substantially in the plane of the femoral paddle 31 and protrudes from an edge of the femoral paddle 31. This femoral arm 32 terminates in a free end which is in the form of a jaw 33 comprising two clamps 34, 35 opposite each other and movable between a clamped position and an unclamped position. The clamps 34, 35 comprise an inner clamp 34 and an outer clamp 35, the inner clamp 34 being located closer to the femoral paddle 31 than the outer clamp 35.

More specifically, the jaw 33 is formed by a slotted slide in which a slot 330 is provided between the two clamps 34, 35, this slot 330 extending in a plane orthogonal to a transverse axis AT which, in turn, is orthogonal to the anterior-posterior axis AP and to the longitudinal axis AL.

Moreover, there is provided a clamping orifice 37 which crosses the two clamps 34, 35, and which therefore also crosses the slot 330, while extending along the transverse axis AT. This clamping orifice 37 presents a smooth portion in the outer clamp 35, and a tapped portion in the inner clamp 4. This clamping orifice 37 opens into a face 350 of the outer clamp 35 which is orthogonal to the transverse axis AT in order to enable the insertion of a clamping screw 38 (shown in FIGS. 4, 11 and 12).

The clamping screw 38 presents a threaded rod engaged into the tapped portion of the clamping orifice 37, and it presents a head provided with an imprint capable of cooperating with a clamping screwdriver 10 (shown in FIG. 11); this head of the clamping screw 38 abutting against an inner shoulder provided in the smooth portion of the clamping orifice 37.

Thus, the clamping screw 38 forms a clamping element cooperating with the jaw 33 so as to displace the clamps 34, 35 between a clamped position (wherein the clamps 34, 35 are brought close to each other and the slot 330 is reduced) and an unclamped position (wherein the clamps 34, 35 are spaced apart and the slot 330 is enlarged in comparison with the clamped position). Thus, screwing of the clamping screw 38 displaces the clamps 34, 35 toward the clamped position and unscrewing of the clamping screw 38 displaces the clamps 34, 35 toward the unclamped position.

The outer clamp 35 presents a notch 351 turned toward the inner clamp 34, and the inner clamp 34 presents a shoulder 341 turned toward the outer clamp 35; the notch 351 and the shoulder 341 thus being opposite each other.

There is also provided a reference marking 36 formed on the outer clamp 35, this reference marking 36 forming a second reference element for measuring a value of the pivot angle of the femoral paddle 31 with respect to the tibial paddle 21.

The femoral element 3 also presents a central stud 39, protruding from an upper face of the femoral paddle 31 and located in a midplane of the femoral paddle 31 including the anterior-posterior axis AP; this upper face being opposite to a lower face which faces the tibial paddle 21. The pivot shaft 30 extends this central stud 39.

This central stud 39 presents, on either side of the midplane, two opposite notches 390 whose shapes define:
  lower keyed connectors for enabling a univocal positioning of a force sensor 8 (described later on) on the upper face of the femoral paddle 31; and
  upper keyed connectors for enabling a univocal positioning of a compensation wedge 7 (described later on) on the upper face of the femoral paddle 31 or on the force sensor 8 when the latter is present.

Referring to FIG. 5, the movable element 4 is formed by an integral part and mainly comprises the guide 40 extending according to the longitudinal axis AL and surmounted by a body 41 extending transversely on either side of the longitudinal axis AL.

The guide 40 is in the form of a rod provided with a rack 42 formed by a series of teeth evenly distributed along the longitudinal axis AL over a portion of the rod, wherein this guide 40 is slidably mounted inside the guide orifice 22 provided in the base 20 of the static tibial element 2.

Moreover, the guide 40 presents a key (not shown) intended to fit into the groove 220 of the guide orifice 22 so as to prevent the rotation of the guide 40 inside the guide orifice 22.

The setting system 5 comprises a pinion 50 which is pivotally mounted on the base 20 of the static tibial element 2 according to a direction parallel to the anterior-posterior axis AP, and which is more specifically pivotally mounted inside the setting orifice 27.

As shown in FIG. 7, this pinion 50 presents:
- a first pinion portion 51 forming part of a reversible locking mechanism, wherein this first pinion portion 51 is in the form of a toothed wheel comprising unidirectional (or asymmetric) teeth at the periphery, and this first pinion portion 51 extends beyond the base 20 at the level of its front face 201;
- a second pinion portion 52 intended to mesh with the rack or series of teeth 42 of the guide 40, wherein this second pinion portion 52 is in the form of a toothed wheel comprising bidirectional (or symmetric) teeth at the periphery.

Figure 11:
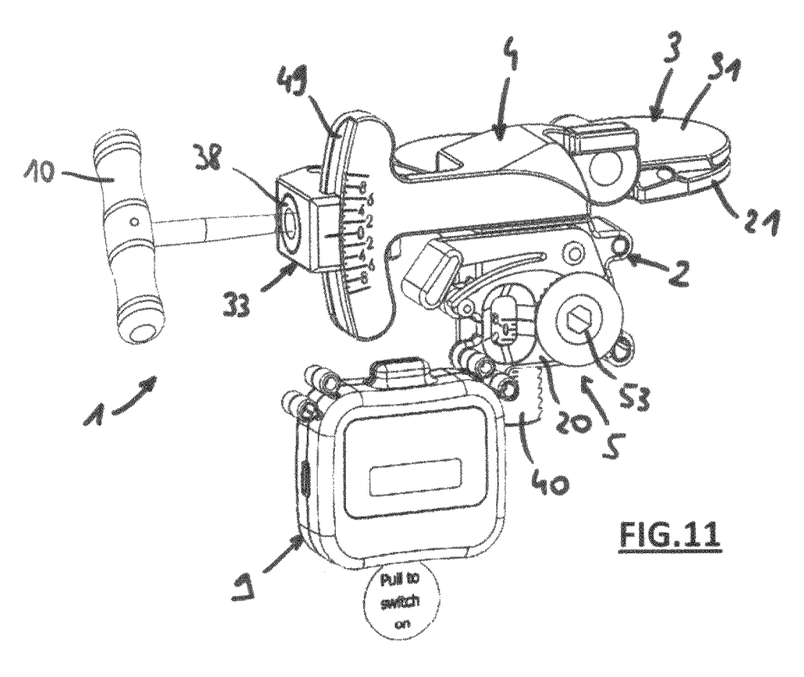
FIG. 11 is a schematic perspective view of the surgical system of FIG. 1, without the guide element, and with a clamping screwdriver.
Figure 12:
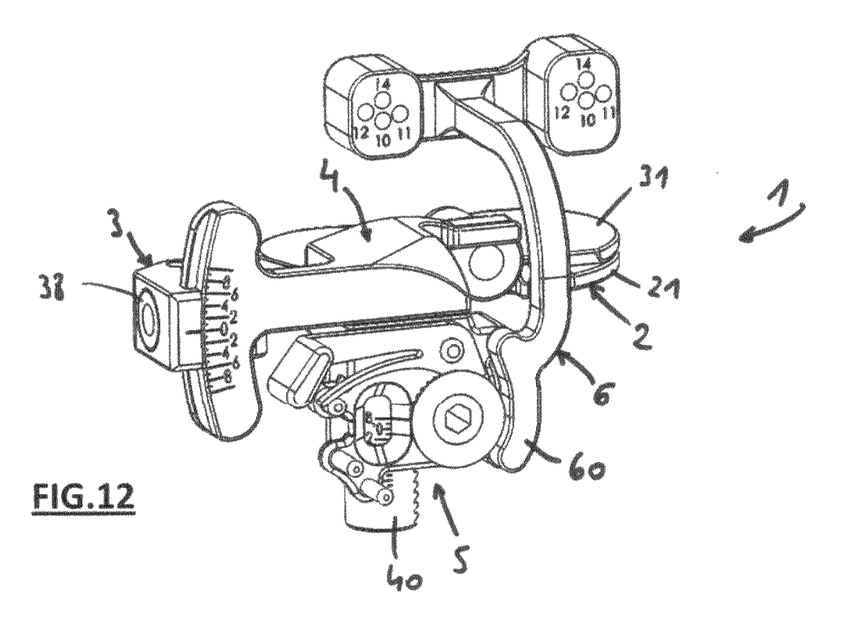
FIG. 12 is a schematic perspective view of the surgical system of FIG. 1, without the force sensor and measuring apparatus set.

The pinion 50 is rotatably secured to a setting screw 53 provided with an imprint capable of cooperating with the aforementioned clamping screwdriver 10 (shown in FIG. 11).

Thus, screwing of the setting screw 53 rotatably displaces the pinion 50 in a first direction of rotation S1, which drives the guide 40 in translation upwardly so as to displace the femoral paddle 31 in the direction of spacing apart away from the tibial paddle 21.

Conversely, unscrewing of the setting screw 53 rotatably displaces the pinion 50 in a second direction of rotation S2 (opposite to the first direction of rotation S1), which drives the guide 40 in translation downwardly so as to displace the femoral paddle 31 in the direction of getting close to the tibial paddle 21, provided that the latch 54 is in an unlocking position as described hereinafter.

Moreover, the guide 40 further presents a scale of graduations 48 distributed along the longitudinal axis AL; this graduated scale 48 forming a first measuring element for measuring a value of the spacing between the femoral paddle 31 and the tibial paddle 21. Indeed, this graduated scale 48 is visible through the aperture 23 provided on the front face 201 of the base 20, and the marking 24 provided at the side of the aperture 23 visually matching with the graduated scale 48, so as to measure a value of the spacing according to the longitudinal axis AL between the femoral paddle 31 and the tibial paddle 21. As example, the graduated scale 48 is graduated every 1 millimeter.

The setting system 5 comprises a reversible locking mechanism coupled between the base 20 of the static tibial element 2 and the pinion 50 so as to reversibly lock the rotation of the pinion 50 and consequently the mobility of the guide 40 relative to the base, in order to set the spacing between the femoral paddle 31 and the tibial paddle 21.

In the illustrated example, the reversible locking mechanism comprises a latch 54 pivotally mounted on the base 20 according to a direction parallel to the anterior-posterior axis AP, and more specifically the latch 54 is pivotally mounted on the first finger 28 provided in protrusion on the front face 201 of the base 20.

The latch 54 is movable between:
- a locking position (shown in FIG. 7) in which the latch 54 cooperates with the pinion 50 so as to rotatably lock it in one direction according to a second direction of rotation S2 (corresponding to a reduction of the spacing between the femoral paddle 31 and the tibial paddle 21), while enabling the rotation of the pinion 50 according to the first direction of rotation S1 (corresponding to an increase of the spacing between the femoral paddle 31 and the tibial paddle 21); and
- an unlocking position in which the latch 54 does not cooperate with the pinion 50 which is then free to pivot in both directions of rotation S1, S2.

More specifically, this latch 54 is provided with a pivot arm 55 provided with a first end on which a pawl 56 is provided capable of blocking into the unidirectional teeth of the first pinion portion 51 of the pinion 50 in the locking position, so as to:
- provide blocking into these unidirectional teeth in order to prevent the rotation of the pinion 50 in the second direction of rotation S2;
- while enabling the rotation of the pinion 50 in the first direction of rotation S1.

The arm 55 of the latch 54 is also provided with a second end, opposite to the first end, on which a bearing surface 57 is provided enabling the surgeon to press atop in order to make the arm 55 pivot in the direction of uncoupling the pawl 56 from the unidirectional teeth of the first pinion portion 51 of the pinion 50, which result in unlocking of the latch 54. Thus, by pressing on this press support 57, the latch 54 is uncoupled from the pinion 50 (unlocking position) which is therefore enabled to turn in both directions of rotation S1, S2.

This latch 54 is also provided with an elastic return member 58 biasing the arm 55 toward the locking position, in other words toward a blocking (or coupling) position of the pawl 56 into the unidirectional teeth of the first pinion portion 51 of the pinion 50. This elastic return member 58 is in the form of a lever secured to the pawl and having a free end which bears on the second finger 29.

The body 41 of the movable element 4, which is secured to an upper end of the guide 40, presents two arms 43, 44 extending transversely to the longitudinal axis AL, on either side of this longitudinal axis AL, with:
- a transverse arm 43 terminating in a free end provided with an arch 45, so that the transverse arm 43 has a «T» like general shape;
- a pivot arm 44 terminating in a free end provided with a pivot hole 47 capable of receiving the femoral element 3 pivotally about the pivot shaft 30, so that the femoral element 3 pivots on this pivot arm 44 according to the anterior-posterior axis AP.

The arch 45 is provided with a scale of graduations 46 distributed around the anterior-posterior axis AP, this graduated scale 46 forming a first reference element for measuring a value of the pivot angle of the femoral paddle 31 with respect to the tibial paddle 21. Indeed, the reference marking 36 formed on the outer clamp 35 of the femoral element 3 is visually aligned with the graduated scale 46, so as to measure a value of the pivot angle of the femoral paddle 31 with respect to the tibial paddle 21. As example, the graduated scale 46 is graduated every 1 degree, between −10 degrees and +10 degrees, the zero angle or 0 degree corresponding to a parallelism between the femoral paddle 31 and the tibial paddle 21.

The arch 45 presents an arcuate outer edge, having a curvature substantially centered on the anterior-posterior axis AP, and in which a rail 49 is provided along which the graduated scale 46 is disposed.

Hence, this rail 49 is provided on the free end of the transverse arm 43 and this rail 49 is intended to fit into the jaw 33 between the two clamps 34, 35, and more specifically this rail 49 is interposed between:

the notch 351 provided on the outer clamp 35, the rail 49 then being blocked by this notch 351; and the shoulder 341 provided on the inner clamp 34.

Thus, the surgical instrument 1 further comprises a reversible blocking system coupled between the transverse arm 43 of the movable element 4 and the femoral arm 32 of the femoral element 3 so as to pivotally immobilize the femoral element 3 with respect to the movable element 4 in a reversible manner in order to set the pivot angle of the femoral paddle 31 with respect to the tibial paddle 21 at different pivot angle values.

This reversible blocking system comprises:

the jaw 33 comprising the two clamps 34, 35 opposite each other and movable between a clamped position and an unclamped position;

the rail 49 engaged into the jaw 33 between the two clamps 34, 35;

the clamping screw 38 which forms a clamping element cooperating with the jaw 33 so as to displace the clamps 34, 35 between the clamped position and the unclamped position.

In the clamped position, the rail 49 is stuck between the two clamps 34, 35 and is therefore blocked, so that the femoral element 3 is pivotally immobilized with respect to the movable element 4.

In the unclamped position, the rail 49 is free to be displaced between the two clamps 34, 35 and it is therefore free to pivot about the anterior-posterior axis AP, so that the femoral element 3 is enabled to pivot relative to the movable element 4. The surgeon can use a clamping screwdriver 10 as a lever arm, once engaged with the clamping screw 38, in order to make the femoral element 3 pivot relative to the movable element 4 when the clamps 34, 35 are in the unclamped position, and then, when he believes that the pivot angle is suitable, all it needs then is to screw the clamping screw 38 and thus clamp the jaw 33 again in the clamped position.

Thus, this clamping screwdriver 10 ensures a dual function:

a lever arm function for pivotally orientating the femoral paddle 31 about the anterior-posterior axis AP;

a clamping function for controlling the closure of the jaw 33.

This surgical instrument 1 may be used with a force sensor 8 adapted to be removably placed on the upper face of the femoral paddle 31, in order to detect one or several force(s) exerted by the condyles of the femur on the femoral paddle 31.

Figures 9, 10:
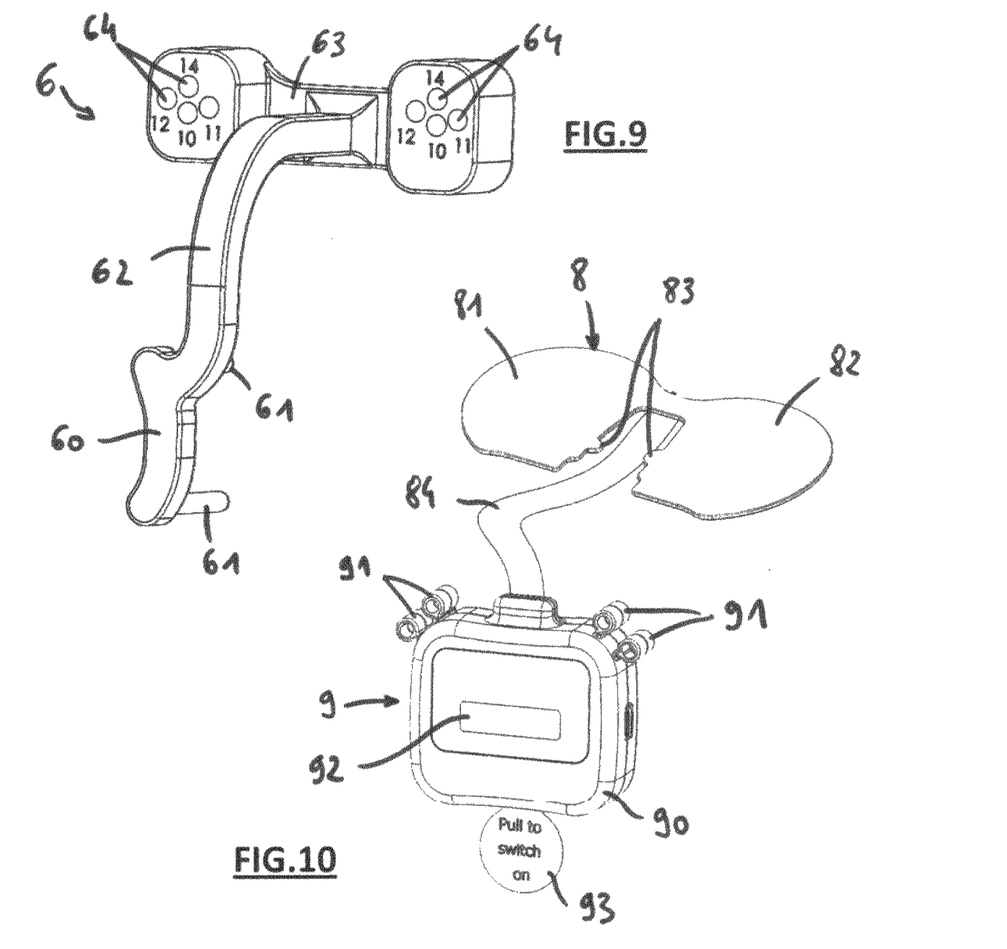
FIG. 9 is a schematic perspective view of the guide element alone for the surgical system of FIG. 1.
FIG. 10 is a schematic perspective view of the force sensor and measuring apparatus set alone for the surgical system of FIG. 1.

As shown in FIG. 10, this force sensor 8 comprises a medial detector 81 intended to detect a force exerted by the medial condyle of the femur on the femoral paddle 31, and a lateral detector 82 intended to detect a force exerted by the lateral condyle of the femur on the femoral paddle 31. The situation may be reversed depending on whether it consists of a right knee or a left knee.

This force sensor 8 is provided with two lugs 83 opposite other and configured to fit into the notches 390 of the central stud 39 of the femoral element 3, in order to be coupled with the lower keyed connectors so as to enable a univocal positioning of this force sensor 8.

This force sensor 8 is connected to a measuring apparatus 9, via a wireless link or via a wired link as in the illustrated example, this wired link being in the form of a connecting ribbon 84. It should be noted that the pivot arm 44 may presents, above the pivot hole 47, a platform 440 serving as a guide or support in order to assist in the positioning of the connecting ribbon 84.

As shown in FIG. 10, this measuring apparatus 9 comprises a case 90 inside which an electric battery and a control unit are provided, not shown, and comprising for example an electronic chip, a processor, a controller and/or an electronic board; this control unit being intended to receive the measurements performed by the force sensor 8.

Moreover, the case 90 presents at its right and left sides, two annular holding barrels 91 capable of receiving the two pins 25 therein in order to enable removable mounting of the measuring apparatus 9 on the base 20 of the static tibial element 2. There are two holding barrels 91, to the right and to the left, in order to adapt to both a right knee dedicated surgical instrument 1 and a left knee dedicated surgical instrument 1.

This measuring apparatus 9 is also provided with a front display 92, providing a display of the measurement performed by the force sensor 9. A turn-on tab 93 is also provided for setting the electric battery and an embedded contactor (not shown) on contact so as to turn on the force sensor 8.

This surgical instrument 1 may be used with a compensation wedge 7 adapted to be removably placed on the upper face of the femoral paddle 31, and in particular on the force sensor 8 when the latter is present.

Figure 8:
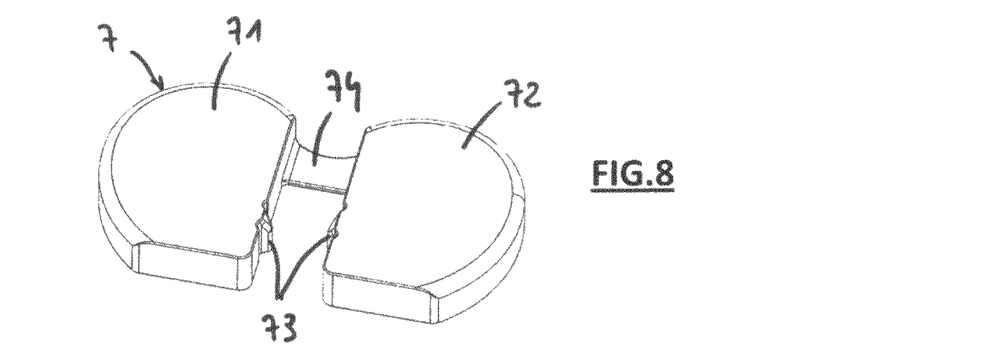
FIG. 8 is a schematic perspective view of the compensation wedge alone for the surgical system of FIG. 1.

As shown in FIG. 8, this compensation wedge 7 comprises a medial compartment 71 provided for supporting the distal medial condyle of the femur, and a lateral compartment 72 provided for supporting the distal lateral condyle of the femur. The medial compartment 71 and the lateral compartment 72 are connected via a central bridge 74. The situation may be reversed depending on whether it consists of a right knee or a left knee.

This compensation wedge 7 is provided with two lugs 73 opposite each other and configured to fit into the notches 390 of the central stud 39 of the femoral element 3, in order to be coupled with the upper keyed connectors (above the lower keyed connectors) so as to enable univocal positioning of this compensation wedge 7.

This surgical instrument 1 may also be used with a guide element 6 forming a positioner for nails that will then serve in fixing one or more femoral cutting guide(s).

As shown in FIG. 9, this guide element 6 is formed into an integral part comprising a basis 60 provided with two holding pins 61 capable of fitting into the two holding holes 26 provided on the base 20 of the static tibial element 2, in order to removably mount this guide element 6 on the base 20.

This guide element 6 comprises an arm 62 extending the basis 60 and terminating in an end secured to a support 63 in which several guide orifices 64 are provided, to the right and to the left, for positioning or guiding drills in the femur; such drills may then serve in fixing the femoral cutting guide(s).

Thus, the guide orifices 64 form drill bushings corresponding to different insert thicknesses and extend in pairs parallel to the bearing plane of the tibial paddle 21 on the resected end of the tibia.

The parallelism of these guide orifices 64 and the control of their positioning via the holding pins 61 allow obtaining a ligament balance at the end of the surgery equivalent to the ligament balance obtained during the use of the surgical instrument 1, consideration being made to possible inaccuracies in cutting and implants positioning.

The following description covers the use of the surgical instrument 1 by a surgeon.

After having performed the tibial cut and the distal femoral cut, and after having set the leg in an extended state, the surgeon inserts the surgical instrument 1, the compensation wedge 7 and the force sensor 8 into the joint. The patella is set back in place.

The rotation of the femoral paddle 21 is possibly locked on a pivot angle value of 0 degree using the locking screw 38 and the clamping screwdriver 10. The display 92 of the measuring apparatus 9 indicates to the surgeon an objective assessment of the ligament tension.

Afterwards, the joint is tensioned with the clamping screwdriver 10 inserted into the setting screw 53 coupled to the pinion 50 until obtaining a tension that the surgeon considers as satisfactory. The value of the spacing between the femoral paddle 31 and the tibial paddle 21 (or distraction value) is indicated by the marking 24 visually matching with the graduated scale 48, and this value corresponds to the thickness of the insert that should be used during the setup of the ultimate implants.

After having set the leg in a bent state, the surgeon inserts the surgical instrument 1 and the force sensor 8 into the joint, and resets the patella back in place.

The rotation of the femoral paddle 21 is unlocked by means of the clamping screwdriver 10 engaged into the locking screw 38, so that the femoral paddle 21 pivots freely about the anterior-posterior axis AP. The display 92 of the measuring apparatus 9 indicates an objective assessment of the ligament tension.

Afterwards, the joint is tensioned with the clamping screwdriver 10 inserted into the setting screw 53 coupled to the pinion 50 until obtaining a tension that the surgeon considers as satisfactory. During tensioning, the femoral paddle 21 pivots freely about the anterior-posterior axis AP which tends the balance the forces. The surgeon may be satisfied with the mechanically-obtained equilibrium or adjust the balance through the lever arm effect offered by the clamping screwdriver engaged with the locking screw 38, the adjustment thereby obtained is fixed by screwing the locking screw 38 until locking the rotation of the femoral paddle 31.

The guide element 6 is then mounted on the base 20 of the static tibial element 2, and the surgeon uses the insert thickness obtained earlier to identify the guide orifices 64 into which drills are performed before screwing two wires for fixing the femoral cutting guide.

Afterwards, the surgical instrument 1, the force sensor 8 and the guide element 6 are extracted from the joint, and the femoral cutting guide is set in place on the two previously screwed wires. Thus, the femoral cuts may be performed and the implants may be set in place. The ligament balance is ultimately reproduced by the implants, consideration being made to possible inaccuracies in cutting and implants positioning.

The invention claimed is:

1. A surgical instrument for knee balancing in the context of a preparation of surgical setting of a total knee prosthesis, said surgical instrument comprising:
    a static tibial element including a base secured to a tibial paddle intended to bear on a resected proximal end of the tibia;
    a femoral element including a femoral paddle intended to bear on the distal or posterior condyles of the femur or on a resected distal end of the femur or on a compensation wedge;
    a movable element including a guide mounted movable in translation on the base of the static tibial element according to a longitudinal axis, and in which the femoral element is pivotally mounted on said movable element according to an anterior-posterior axis, so that the femoral paddle pivots about said anterior-posterior axis relative to the tibial paddle which is static; and
    a setting system coupled between the guide of the movable element and the base of the static tibial element for setting the mobility of said guide relative to said base in order to provide a distraction function while enabling a setting of the spacing between the femoral paddle and the tibial paddle,
    wherein the movable element comprises a transverse arm secured to the guide, and the femoral element comprises a femoral arm secured to the femoral paddle,
    and wherein the surgical instrument further comprises a reversible blocking system coupled between the transverse arm of the movable element and the femoral arm of the femoral element to pivotally immobilize the femoral element with respect to the movable element in a reversible manner in order to set the pivot angle of the femoral paddle with respect to the tibial paddle at different pivot angle values, wherein the reversible blocking system comprises:
        a jaw which is provided on a free end of the femoral arm, and which comprises two clamps opposite each other and movable between a clamped position and an unclamped position;
        a rail which is provided on a free end of the transverse arm of the movable element and which is engaged into the jaw between the two clamps; and
        a clamping element cooperating with the jaw so as to displace the clamps between the clamped position and the unclamped position, such that, when in the clamped position, the femoral element is pivotally immobilized with respect to the movable element, and, when in the unclamped position, the femoral element is enabled to pivot relative to the movable element.

2. The surgical instrument according to claim 1, wherein the transverse arm of the movable element terminates with a first reference element, and the femoral arm of the femoral element terminates with a second reference element, wherein the first reference element and the second reference element comprise a scale of graduations distributed around the anterior-posterior axis and a reference marking visually matching with the graduated scale, so as to measure a value of the pivot angle of the femoral paddle with respect to the tibial paddle.

3. The surgical instrument according to claim 1, wherein the jaw is formed by a slotted slide in which a slot is provided between the two clamps.

4. The surgical instrument according to claim 1, wherein the clamping element comprises a clamping screw screwed into a clamping orifice which crosses the two clamps, so that screwing of the clamping screw displaces the clamps toward the clamped position and unscrewing of the clamping screw displaces the clamps toward the unclamped position.

5. The surgical instrument according to claim 4, wherein the clamping screw and the clamping orifice extend according to a transverse axis orthogonal to the anterior-posterior axis.

6. A surgical system comprising a surgical instrument according to claim 4, and further comprising a clamping screwdriver capable of cooperating with the clamping screw so as to ensure the screwing/unscrewing thereof, and also capable of forming a lever arm, once engaged with the clamping screw, in order to make the femoral element pivot relative to the movable element when the clamps are in the unclamped position.

7. The surgical instrument according to claim 1, wherein the guide comprises a rack formed by a series of teeth, and the setting system comprises a pinion which is pivotally mounted on the base of the static tibial element and which meshes with the rack.

8. The surgical instrument according to claim 7, wherein the setting system comprises a reversible locking mechanism coupled between the base of the static tibial element and the pinion so as to reversibly lock the rotation of the pinion and consequently the mobility of the guide relative to the base, in order to set the spacing between the femoral paddle and the tibial paddle.

9. The surgical instrument according to claim 8, wherein the reversible locking mechanism comprises a latch movably mounted on the base of the static tibial element between a locking position in which the latch cooperates with the pinion so as to rotatably lock it, and an unlocking position in which the latch does not cooperate with the pinion which is free to pivot.

10. The surgical instrument according to claim 7, wherein:
the guide is provided with a first measuring element;
the base of the static tibial element presents an aperture through which the first measuring element of the guide is visible, and said base further presents a second measuring element placed at the aperture side;
the first measuring element and the second measuring element comprise a scale of graduations distributed along the longitudinal axis and a reference marking visually matching with the graduated scale, so as to measure a value of the spacing between the femoral paddle and the tibial paddle.

11. A surgical system comprising a surgical instrument according to claim 1, and further comprising a force sensor adapted to be removably placed on an upper face of the femoral paddle, opposite to a lower face which faces the tibial paddle, in order to detect one or several force(s) exerted by the condyles of the femur on the femoral paddle.

12. The surgical system according to claim 11, further comprising a measuring apparatus connected to the force sensor, via a wireless or wired link, and intended to receive the measurements performed by the force sensor, wherein said measuring apparatus is removably mounted on the base of the static tibial element.

13. A surgical system comprising a surgical instrument according to claim 1, and further comprising a guide element removably mounted on the base of the static tibial element, said guide element comprising several guide orifices for drills in the femur.

* * * * *